US008168171B2

(12) United States Patent
Mogna et al.

(10) Patent No.: US 8,168,171 B2
(45) Date of Patent: *May 1, 2012

(54) FOLIC ACID PRODUCING BIFIDOBACTERIUM BACTERIAL STRAINS, FORMULATIONS AND USE THEREOF

(75) Inventors: Giovanni Mogna, Novara (IT); Gian Paolo Strozzi, Novara (IT)

(73) Assignee: Probiotical S.p.A., Novara (IT)

( * ) Notice: Subject to any disclaimer, the term of this patent is extended or adjusted under 35 U.S.C. 154(b) by 727 days.

This patent is subject to a terminal disclaimer.

(21) Appl. No.: 11/659,058

(22) PCT Filed: Aug. 5, 2004

(86) PCT No.: PCT/IT2004/000444
§ 371 (c)(1),
(2), (4) Date: Nov. 25, 2008

(87) PCT Pub. No.: WO2006/013588
PCT Pub. Date: Feb. 9, 2006

(65) Prior Publication Data
US 2009/0081167 A1    Mar. 26, 2009

(51) Int. Cl.
*A01N 63/00* (2006.01)
(52) U.S. Cl. ..................................................... 424/93.4
(58) Field of Classification Search .................. None
See application file for complete search history.

(56) References Cited

U.S. PATENT DOCUMENTS

| | | | |
|---|---|---|---|
| 5,614,501 A | 3/1997 | Richards | |
| 6,087,092 A | 7/2000 | Richards | |
| 6,468,525 B1 * | 10/2002 | Watson et al. | 424/93.3 |
| 6,524,574 B1 | 2/2003 | Spangler et al. | |
| 6,841,149 B1 | 1/2005 | Spangler et al. | |
| 2001/0014322 A1 | 8/2001 | Chen et al. | |
| 2009/0081167 A1 | 3/2009 | Mogna et al. | |
| 2009/0087418 A1 | 4/2009 | Strozzi et al. | |

FOREIGN PATENT DOCUMENTS

| | | |
|---|---|---|
| JP | 6217761 A | 8/1994 |
| WO | 9603150 | 2/1996 |
| WO | WO 99/59413 | 11/1999 |
| WO | 2006013588 | 2/2006 |
| WO | 2007054989 A1 | 5/2007 |

OTHER PUBLICATIONS

Yoriko Deguchi et al., "Comparative Studies on Synthesis of Water-soluble Vitamins among Human Species of Bifidobacteria", Agricultural and Biological Chemistry, vol. 49, No. 1, 1985, pp. 13-19, XP009040803, ISSN: 0002-1369.
Linda J. Krause et al., "Feeding Human Milk to Rats Increases Bifidobacterium in the Cecum and Colon Which Correlates with Enhanced Folate Status", American Institute of Nutrition, Journal of Nutrition, vol. 126, No. 5, 1996, pp. 1505-1511, XP009040718, ISSN: 0022-3166.
Wilbert Sybesma et al., "Effects of Cultivation Conditions on Folate Production by Lactic Acid Bacteria", American Society for Microbiology, Applied and Environmental Microbiology, Aug. 2003, vol. 69, No. 8, pp. 4542-4548, XP002308563, ISSN: 0099-2240.
Database WPI Week 199436 Thompson Scientific, Nisshin Flour Milling Co, Aug. 9, 1994 (XP002607276), pp. 1-2.
Marx, et al., "Metabolization of Beta-(2,6)-Linked Fructose-Oligosaccharides by Different Bifidobacteria", Fems Microbiology Letters, 2000, vol. 182, No. 1, pp. 163-169.
McKellar, et al., "Metabolism of Fructo-Oligosaccharides by Bifidobacterium-SSP", Applied Microbiology and Biotechnology, vol. 31, No. 5-6, 1989, pp. 537-541.
Corradini, et al., "High-Performance Anion-Exchange Chromatography Coupled With Pulsed Amperometric Detection and Capillary Zone Electrophoresis With Indirect Ultra Violet Detection As Powerful Tools to Evaluate Prebiotic Properties of Fructooligosaccharides and Inulin", Journal of Chromatography, October 29, 2004, vol. 1054, No. 1-2, pp. 165-173.
Yamazaki, et al., "Purification of Jerusalem Artichoke Fructans and Their Utilization by Bifidobacteria", Journal of the Science of Food and Agriculture, 1994, vol. 64, No. 4, pp. 461-465.

* cited by examiner

*Primary Examiner* — Suzanne M Noakes
(74) *Attorney, Agent, or Firm* — Pearne & Gordon LLP

(57) ABSTRACT

The present invention relates to folic acid-producing bacterial strains belonging to the genus *Bifidobacterium*, pharmaceutical, veterinary or food formulations containing them and the use thereof. In particular, the invention relates to new bacterial strains of human origin belonging to the genus *Bifidobacterium, adolescentis* species (2), the genus *Bifidobacterium, breve* species (1) and the genus *Bifidobacterium, pseudocatenulatum* species (2) deposited in the DSMZ collection center (Deutsche Sammlung von Mikroorganismen und Zellkulturen GmbH; Braunsweig, Germany), in accordance with the Treaty of Budapest, on 21 Jul. 2004.

16 Claims, No Drawings

** FOLIC ACID PRODUCING BIFIDOBACTERIUM BACTERIAL STRAINS, FORMULATIONS AND USE THEREOF

SUMMARY OF THE INVENTION

The present invention relates to folic acid-producing bacterial strains belonging to the genus *Bifidobacterium*, pharmaceutical, veterinary or food formulations containing them and the use thereof.

In particular, the invention relates to new bacterial strains of human origin belonging to the genus *Bifidobacterium, adolescentis* species (2), the genus *Bifidobacterium, breve* species (1) and the genus *Bifidobacterium, pseudocatenulatum* species (2) deposited in the DSMZ collection center (Deutsche Sammlung von Mikroorganismen und Zellkulturen GmbH; Braunsweig-Germany), in accordance with the Treaty of Budapest, on 21 Jul. 2004.

The aforesaid strains were respectively ascribed the following identification codes:
*Bifidobacterium, adolescentis* species, code DSM 16594;
*Bifidobacterium, adolescentis* species, code DSM 16595;
*Bifidobacterium, breve* species, code DSM 16596;
*Bifidobacterium, pseudocatenulatum* species, code DSM 16597;
*Bifidobacterium, pseudocatenulatum* species, code DSM 16598.

FIELD OF THE INVENTION

Folic acid is an important water-soluble B vitamin that accepts one unit of carbon from a donor molecule.

Thanks to this characteristic, folic acid is central to a large number of essential cellular processes, including, for example, the biogenesis of methyl groups and synthesis of nucleotides, vitamins and several amino acids.

In the body, DNA replication, repair and methylation become more efficient as the availability of folic acid increases.

For this reason, tissues displaying a high proliferation and turnover rate, such as leukocytes, erythrocytes and enterocytes, require a large quantity of folic acid, or at least a good, constant availability thereof.

In humans, folic acid deficiency has been associated with an elevated increase in the risk of cancer: for example, epidemiological studies have shown that the risk of developing a breast tumor after menopause is higher in women with a low folic acid intake.

Conversely, high quantities of folic acid reduce the risk of colorectal cancer.

Folic acid (together with its salts, the folates) plays, among other things, a fundamental role for the cells making up the colorectal mucous membrane, which undergoes a continuous process of epithelial renewal. The role played by folic acid in preventing colorectal cancer has been described in the literature (Ref. 1). It has been demonstrated, in particular, that polymorphisms of genes responsible for the metabolism of the methyl group are associated with the familial risk of colorectal cancer and that the effect of these genes is modified by the availability of folates (Ref. 2).

Consequently, a low or diminished local availability of folic acid may result in DNA hypomethylation, thus favoring, for example, the occurrence of colon cancer.

Furthermore, the availability of large quantities of folic acid is recommended for patients affected with inflammatory bowel diseases (IBD), since it helps regulate the proliferation of cells in the colon and rectum.

It is thus of utmost importance to find a means by which to endow the body with a natural, non-toxic endogenous source capable of supplying the necessary quantity of folic acid on a continuous basis and thus providing an alternative to the conventional systemic methods of administration of said substance, or the salts thereof.

Unfortunately, up to now no type of solution has been found to meet this necessity.

It is well known that the human colon is colonized by a complex and numerous microbial community that actively interacts with the host.

The concentration of bacteria in the colon is approximately $10^{11}$-$10^{12}$ bacteria per gram of intestinal content.

There are at least 400 bacterial species present, but 30-40 species on their own account for approximately 95-98% of total microflora.

Among these principal species, those belonging to the genus *Bifidobacterium* represent one of the major intestinal microbial groups present in man. *Bifidobacterium* is a genus known for its beneficial activity within the body. This activity translates, for example, into the following effects: ability to replenish intestinal bacterial flora following antibiotic therapy, maintenance of a balance among the various intestinal microbial groups, reduction in serum cholesterol levels, production of vitamins, alleviation of lactose intolerance and immunomodulation.

The bacteria belonging to the *Bifidobacterium* genus are therefore rightly considered probiotics and commonly used as such in the pharmaceutical, veterinary and/or food sectors.

A probiotic is by definition a live microbial supplement whose activity is beneficial to human or animal health.

To date, no probiotic strains have been known to produce folic acid (folic acid-producing bacteria belonging to the genera *Lactobacillus* and *Lactococcus* have been described, but they have not been proposed as probiotics).

In particular, no probiotic bacteria of the *Bifidobacterium* genus have been known to develop in a culture medium completely devoid of folic acid and produce the latter in large quantities.

DESCRIPTION OF THE INVENTION

The Applicant unexpectedly found that strains of probiotic bacteria of human origin, belonging to the *Bifidobacterium* genus, are producers of folic acid. Folic acid-producing strains belonging to the following species, for example, were identified: *Bifidobacterium longum, Bifidobacterium infantis, Bifidobacterium adoloscentis, Bifidobacterium bifidum, Bifidobacterium breve, Bifidobacterium angulatum, Bifidobacterium catenulatum, Bifidobacterium pseudocatenulatum, Bifidobacterium gallicum, Bifidobacterium dentium, Bifidobacterium denticolens, Bifidobacterium inopinatum, Bifidobacterium animalis, Bifidobacterium lactis.*

Among these strains of bacteria, the species *Bifidobacterium adoloscentis, Bifidobacterium breve* and *Bifidobacterium pseudocatenulatum* have shown to be particularly interesting, as described in detail below and in the appended claims.

More specifically, in a preferred aspect of the invention, as described in detail below and in the appended claims, the Applicant isolated and deposited in the DSMZ (Deutsche Sammlung von Mikroorganismen und Zellkulturen GmbH; Braunsweig-Germany), on 21 Jul. 2004, five new bacterial strains of human origin belonging to the genus *Bifidobacterium*. Of these five new bacterial strains, two belong to the species *Bifidobacterium adoloscentis*, one to the species *Bifidobacterium breve*, and two to the species *Bifidobacterium*

*pseudocatenulatum*. Said strains were respectively ascribed the following identification codes:

DSM 16594;
DSM 16595;
DSM 16596;
DSM 16597;
DSM 16598.

Said bacterial strains were taxonomically and technologically characterized, as described below, and showed to produce large quantities of folic acid.

In fact, said strains are capable of developing in a culture medium devoid of folic acid.

In particular, said strains are capable of producing, respectively, the following quantities of folic acid: 56-62, 16-20, 6-9, 14-16 and 14-19 ng/ml of culture medium.

Furthermore, it was unexpectedly observed that the biosynthesis of folic acid by the bacterial strains of the invention is not subject to any negative regulation mechanism (negative feedback) on the part of the resulting product, or any other product already present in the culture medium.

In other words, in physiological conditions, the production of folic acid remains constant regardless of whether the latter is present in the environment.

Finally, it was also observed that changes in pH, typical of the ecosystem of the colon (pH values varying between approximately 7 and 5 are considered likely, in relation to certain pathologies or type of diet), do not negatively impact the productivity of the strains of the present invention.

Microorganisms of this type are therefore able to combine their known probiotic characteristics (thus beneficial to the body) with a capacity for in situ folic acid production (for example in the colon).

Consequently, these strains unexpectedly presented themselves as the desired solution for the technical problem of the present invention, as outlined above.

In fact, said microorganisms represent an ideal, natural, non-toxic endogenous source of folic acid.

The use of suitable formulations containing the folic acid-producing bifidobacteria of the present invention may thus enable continuous in situ production of folic acid.

The probiotic bacteria of the present invention may be administered in a variety of ways, according to patient or consumer needs.

In a preferred aspect, the present invention is aimed at pharmaceutical, veterinary and/or food formulations comprising at least one of the bacterial strains of the present invention or a mixture thereof.

Particularly preferred are formulations comprising at least one of the strains DSM 16594, DSM 16595, DSM 16596, DSM 16597 and DSM 16598 or any combination thereof.

In another preferred aspect, the strains of the present invention can also be formulated in combination with other probiotic bacterial strains having complementary characteristics, i.e. different intrinsic properties.

An example, which should not be construed as limiting, of such formulations may be represented by at least one of the bacterial strains of the present invention in a suitable mixture with a probiotic bacterial strain having the characteristic of strongly adhering to the intestinal mucous membrane.

The strains of the present invention may also be formulated in combination with other strains that, in addition to the intrinsic beneficial characteristics associated with the bacterial genus to which they belong, display other peculiar characteristics useful for the host's health.

Said mixed formulations are able to combine a number of probidtic properties in a single formulation, thereby providing the body with a plurality of benefits, as well as potential synergies deriving therefrom, in a single administration.

In light of the above considerations, it is evident that those skilled in the art will be able to devise many combinations of probiotic bacteria based on their own experience.

Such combinations also fall, therefore, within the scope of the present invention.

By way of example, without restricting the scope of the invention, said probiotic bacteria can be selected from, among others, the genus *Lactobacillus*, including such species as *Lactobacillus bulgaricus, Lactobacillus acidophilus, Lactobacillus casei* subsp. *rhamnosus, Lactobacillus casei* subsp. *paracasei, Lactobacillus plantarum, Lactobacillus fermentum, Lactobacillus salivarius* subsp. *salivarius* and *Lactobacillus pentosus*, or from the genus *Streptococcus*, including such species as *Streptococcus delbrueckii* subsp. *Thermophilus*.

Among these, the particularly preferred strains have shown to include, for example, the following:

*Lactobacillus acidophilus* LMG P-21381 (deposited in the Belgian Coordinated Collections of Microorganisms—BCCM LMG Collection on 31 Jan. 2002);

*Lactobacillus casei* subsp. *paracasei* LMG P-21380 (deposited in the Belgian Coordinated Collections of Microorganisms—BCCM LMG Collection on 31 Jan. 2002);

*Lactobacillus plantarum* LMG P-21021 (deposited in the Belgian Coordinated Collections of Microorganisms—BCCM LMG Collection on 16 Oct. 2002);

*Lactobacillus pentosus* LMG P-21019 (deposited in the Belgian Coordinated Collections of Microorganisms—BCCM LMG Collection on 16 Oct. 2002);

*Lactobacillus plantarum* LMG P-21020 (deposited in the Belgian Coordinated Collections of Microorganisms—BCCM LMG Collection on 16 Oct. 2002);

*Lactobacillus plantarum* LMG P-21022 (deposited in the Belgian Coordinated Collections of Microorganisms—BCCM LMG Collection on 16 Oct. 2002);

*Lactobacillus plantarum* LMG P-21023 (deposited in the Belgian Coordinated Collections of Microorganisms—BCCM LMG Collection on 16 Oct. 2002);

*Bifidobacterium lactis* LMG P-21384 (deposited in the Belgian Coordinated Collections of Microorganisms—BCCM LMG Collection on 31 Jan. 2002);

*Streptococcus delbrueckii* subsp. *thermophilus* DSM 16506 (deposited in the DSMZ on 18 Jun. 2004);

*Streptococcus delbrueckii* subsp. *thermophilus* DSM 16507 (deposited in the DSMZ on 18 Jun. 2004);

*Bifidobacterium longum* DSM 16603 (deposited in the DSMZ on 20 Jul. 2004);

*Bifidobacterium breve* DSM 16604 (deposited in the DSMZ on 20 Jul. 2004);

*Lactobacillus casei* subsp. *rhamnosus* DSM 16605 (deposited in the DSMZ on 20 Jul. 2004);

Consequently, particularly preferred mixed formulations of the invention will comprise at least one of the bacterial strains from DSM 16594 to DSM 16598, or any mixture thereof, appropriately formulated in combination with at least one of the probiotic bacterial strains listed above, or any mixture thereof.

Preferably, said probiotic bacterial strains are selected from the group comprising:

*Lactobacillus acidophilus* LMG P-21381;
*Lactobacillus casei* subsp. *paracasei* LMG P-21380;
*Lactobacillus plantarum* LMG P-21021;
*Lactobacillus pentosus* LMG P-21019;
*Lactobacillus plantarum* LMG P-21020;

*Lactobacillus plantarum* LMG P-21022;
*Lactobacillus plantarum* LMG P-21023;
*Bifidobacterium lactis* LMG P-21384;
*Streptococcus delbrueckii* subsp. *thermophilus* DSM 16506;
*Streptococcus delbrueckii* subsp. *thermophilus* DSM 16507;
*Bifidobacterium longum* DSM 16603;
*Bifidobacterium breve* DSM 16604;
*Lactobacillus casei* subsp. *rhamnosus* DSM 16605.

The number and type of bacterial strains to be combined in said mixed formulations will be decided by those skilled in the art according to the type and severity of the pathology to be treated or prevented, or the type of probiotic food product one wishes to obtain.

In another preferred aspect, the bacterial strains of the present invention, used singly or in combination with one another and/or with other probiotic bacterial strains, may be further formulated in combination with other substances having prebiotic properties.

Preferably, said substances having prebiotic properties comprise, in particular, carbohydrates that are not digested and absorbed by man and thus reach the colon completely intact, where they selectively stimulate the development and activity of a number of beneficial microbial groups, bifidobacteria in particular.

Particularly preferred among said prebiotic carbohydrates are those selected from the group comprising: fructo-oligosaccharides (FOS), in particular inulin, isomalto-oligosaccharides, resistant starch, pectin, galacto-oligosaccharides (GOS), arabinogalactan, xylo-oligosaccharides (XOS), chitosan oligosaccharides (COS) and glucomannan.

By way of example, without restricting the scope of the invention, preferred formulations comprise at least one of the bacterial strains from DSM 16594 to DSM 16598, or any mixture thereof, appropriately formulated in combination with at least one substance having prebiotic properties selected, for example, from among those listed above, i.e. fructo-oligosaccharides (FOS), in particular inulin, isomalto-oligosaccharides, resistant starch, pectin, galacto-oligosaccharides (GOS), arabinogalactan, xylo-oligosaccharides (XOS), chitosan oligosaccharides (COS) and glucomannan.

Preferred formulations of the invention likewise comprise at least one of the bacterial strains from DSM 16594 to DSM 16598, or any mixture thereof, appropriately formulated in combination with at least one of the probiotic bacterial strains listed above, or any mixture thereof, and with at least one substance having prebiotic properties selected, for example, from among those listed above, i.e. fructo-oligosaccharides (FOS), in particular inulin, isomalto-oligosaccharides, resistant starch, pectin, galacto-oligosaccharides (GOS), arabinogalactan, xylo-oligosaccharides (XOS), chitosan oligosaccharides (COS) and glucomannan.

Preferably, said probiotic bacterial strains are selected from the group comprising:
*Lactobacillus acidophilus* LMG P-21381;
*Lactobacillus casei* subsp. *paracasei* LMG P-21380;
*Lactobacillus plantarum* LMG P-21021;
*Lactobacillus pentosus* LMG P-21019;
*Lactobacillus plantarum* LMG P-21020;
*Lactobacillus plantarum* LMG P-21022;
*Lactobacillus plantarum* LMG P-21023;
*Bifidobacterium lactis* LMG P-21384;
*Streptococcus delbrueckii* subsp. *thermophilus* DSM 16506;
*Streptococcus delbrueckii* subsp. *thermophilus* DSM 16507;
*Bifidobacterium longum* DSM 16603;
*Bifidobacterium breve* DSM 16604;
*Lactobacillus casei* subsp. *rhamnosus* DSM 16605.

The preferred embodiments of the present invention include those formulations wherein the strains of the invention are preferably employed in freeze-dried form.

The strains of the invention are preferably formulated in combination with appropriate vehicles, excipients, flavorings, stabilizers and additives, such as amino acids, vitamins, antioxidants and enzymes, commonly used in the preparation of pharmaceutical and/or food formulations.

Solely by way of example, without restricting the scope of the invention, among the particularly preferred additives there can be mentioned glutamine, arginine, superoxide dismutase and glutathione.

The formulations of the present invention may be administered orally, with suppositories, or with vaginal tablets or capsules, as such or in combination with food products like, for example, milk, yogurt, milk derivatives or fermented milk products, for the treatment and/or prevention of gastrointestinal disorders (diarrhea, antibiotic therapy, IBD, prevention of colon cancer) where it is desirable to administer an adequate quantity of folic acid.

As noted above, the formulations of the present invention can also be administered following or during antibiotic therapies in order to replenish and restore the balance of non-pathogenic intestinal flora.

Particularly preferred formulations are those to be administered orally, by means of suppositories or vaginal capsules or tablets.

Typical forms of formulation include, for example, capsules, oral solutions or suspensions, powders contained in packets or analogous forms, tablets, suppositories and pessaries.

As to dosage, each formulation will normally contain from $10^5$ to $10^{11}$ cells of each bacterial strain per single dose, preferably from $10^6$ to $10^{11}$ bacteria per dose, most preferably from $10^7$ to $10^{10}$ bacteria per dose.

In general, the concentration of the active principle, or of the mixture of active principles, may range from $10^8$ cells of bacterial strain(s) per gram of formulation to $10^{11}$ cells per g; preferably from $10^9$ cells per g to $10^{10}$ cells per g of formulation.

One example of the potential applications of the present invention, which in no way restricts the scope thereof, regards a case in which the strains of the invention were administered to an adult patient undergoing antibiotic therapy.

For the entire duration of the antibiotic therapy and for five days following its termination said patient received two packets per day of a freeze-dried formulation of DSM 16594 and DSM 16595 in combination with the probiotic strains DSM 16506 and LMG P-21380 and with glutamine.

The contents of each packet, administered in the form of an oral suspension in water, comprised approximately $10^{10}$ cells of each bacterial strain and, as excipients, starch, tween, dispersants mandarin flavouring, acesulfame, saccharine, ascorbic acid and methyl parabene.

The bacterial strains of the present invention have also demonstrated to be particularly useful for enhancing the nutritional value of foodstuffs.

Particularly preferred foodstuffs are those derived from milk and/or its derivatives, for example yogurt and fermented milk as well as snack fillings, ice-cream and so forth.

DETAILED DESCRIPTION OF THE INVENTION

Isolation of the Strains

The strain *Bifidobacterium adolescentis* DMS 16594 was isolated from the feces of an adult subject who had taken neither antibiotics nor probiotic preparations in the 3 months prior to the isolation.

A 10% suspension of fresh feces was prepared in Wilkins-Chalgren Anaerobe Broth (Oxoid Limited, Basingstoke, Hampshire, England, UK) at a concentration of 0.5×, i.e. by preparing a 1:1 dilution of the medium obtained according to the directions on the package.

Serial dilutions up to $10^{-9}$ were made from the homogenate (1:10 dilutions, obtained by diluting 1 ml of the previous dilution in 9 ml of the same medium). 0.1 ml aliquots of the dilutions between $10^{-6}$ and $10^{-9}$ were plated in a selective medium for bifidobacteria, RB agar (Ref. 3).

The plates were incubated in anaerobiosis at 37° C. for 48 hours.

All the preparations were made in an anaerobic chamber (Equipment: Anaerobic System, Mod. 2028, Form a Scientific Co., Marietta, Ohio) in the following atmosphere: $N_2$ 85%, $CO_2$ 10%, $H_2$ 5%.

The colony corresponding to bacterial strain DMS 16594 was isolated among those producing a yellow halo, due to the acidification of the medium and color change of the indicator.

Attribution to the Genus *Bifidobacterium* and to the Species *Bifidobacterium adolescentis*

For the purpose of attributing DMS 16594 to the genus *Bifidobacterium*, genus-specific amplification was performed using 16S rDNA-targeted primers Bif164/Bif662, from which corrected amplicon of 523 bp was obtained. In parallel, a biochemical assay was performed to identify the key enzyme of bifidobacteria carbohydrate metabolism, i.e. fructose-6-phosphate phosphoketolase.

The adolescentis species was identified by DNA-DNA hybridization, as described in the paper by Scardovi et al. (Ref. 4).

Characteristics of Strain DMS 16594

| | |
|---|---|
| Origin: | human |
| Age: | 39 |
| Sex: | F |
| Genus: | *Bifidobacterium* |
| Species: | *adolescentis* |
| Morphology: | irregular rods, at times bifid in form, with protuberances and swellings |
| Folic acid production: | between 56 and 62 ng/ml |
| Plasmids: | no |

The other bacterial strains, DSM 16595, DSM 16596, DSM 16597 and DSM 16598, were isolated using a procedure similar to the one described above.

Characteristics of Strain DSM 16595

| | |
|---|---|
| Origin: | human |
| Age: | 37 |
| Sex: | F |
| Genus: | *Bifidobacterium* |
| Species: | *adolescentis* |
| Morphology: | irregular rods, at times bifid in form, with protuberances and swellings |
| Folic acid production: | between 16 and 20 ng/ml |
| Plasmids: | no |

Characteristics of Strain DMS 16596

| | |
|---|---|
| Origin: | human |
| Age: | 39 |
| Sex: | F |
| Genus: | *Bifidobacterium* |
| Species: | *breve* |
| Morphology: | short irregular rods |
| Folic acid production: | between 6 and 9 ng/ml |
| Plasmids: | no |

Characteristics of Strain DMS 16597

| | |
|---|---|
| Origin: | human |
| Age: | 56 |
| Sex: | M |
| Genus: | *Bifidobacterium* |
| Species: | *pseudocatenulatum* |
| Morphology: | irregular rods |
| Folic acid production: | between 14 and 16 ng/ml |
| Plasmids: | yes, one of approximately 9 kb |

Characteristics of Strain DMS 16587

| | |
|---|---|
| Origin: | human |
| Age: | 56 |
| Sex: | M |
| Genus: | *Bifidobacterium* |
| Species: | *pseudocatenulatum* |
| Morphology: | irregular rods |
| Folic acid production: | between 14 and 19 ng/ml |
| Plasmids: | yes, one of approximately 9 kb |

Strain Development Conditions

The preferred bacterial strains of the present invention, DSM 16594, DSM 16595, DSM 16596, DSM 16597 and DSM 16598, were preserved in stab cultures, i.e. agar stab cultures (10 ml tubes containing 10 ml of 0.9% agarized medium) or in MRS liquid cultures (Bacto Lactobacilli MRS Broth [0881-17] Difco Laboratories, Division of Becton Dickinsons and Company, Sparks, Md. 21152 USA) to which cysteine was added (0.05%).

The medium, prepared according to the directions on the package, was sterilized at 110° C. for 30'.

When the strains are cultured in an ambient without folic acid, a so-called minimum synthetic medium is used; it is identified as No. 7 and has the composition described below.

Said medium is prepared by mixing the components and solutions in the order indicated, under agitation, at room temperature.

The medium is prepared fresh each time.

Minimum Culture Medium No. 7

| | |
|---|---|
| Glucose | 20 g/L |
| Vitamin Assay Casaminoacids (DIFCO Laboratories, USA [0288-17] | 5 g/L |
| Urea | 2 g/L |
| Cysteine | 0.5 g/L |
| Solution A | 700 ml/L |
| Solution B | 1 ml/L |
| Solution C | 1 ml/L |
| Solution D | 5 ml/L |

Solutions A, B, C and D have the Following Composition:

| Solution A | |
|---|---|
| $(NH_4)_2SO_4$ | 10 g |
| Sodium acetate | 10 g |
| Ascorbic acid | 10 g |
| $KH_2PO_4$ | 1 g |
| $MgSO_4$ | 0.7 g |
| NaCl | 0.2 g |
| Tween 80 | 1 ml |

The Tween 80 is dissolved in 700 ml of boiling distilled water; thereafter all the other components are added in sequence.

| Solution B | |
|---|---|
| Boric acid | 25 mg |
| $CuSO_4$ | 2 mg |
| KI | 5 mg |
| $FeCl_3$ | 10 mg |
| $MnSO_4$ | 20 mg |
| Sodium molybdate | 10 mg |
| $ZnSO_4$ | 20 mg |

These components are dissolved in sequence in 50 ml of distilled water at room temperature.

| Solution C | |
|---|---|
| Biotin | 0.2 mg |
| Calcium pantothenate | 40 mg |
| Niacin | 40 mg |
| P-aminobenzoic acid | 20 mg |
| Pyridoxine | 40 mg |
| Riboflavin | 20 mg |
| Thiamine | 40 mg |

These components are dissolved in 100 ml of distilled water at room temperature.

| Solution D | |
|---|---|
| $FeSO_4$ | 50 mg |

The salt is dissolved in 25 ml of distilled water.

The medium is dispensed into 10 ml tubes and sterilized at 100° C. for 30'.

Microbiological Assay of the Folic Acid Produced by Strain DSM 16594

The quantity of folic acid produced in fermentation by strain DSM 16594, as well as by the other strains of the invention, was determined by microbiological assay.

The cultures used for the determination of folic acid productivity were transplanted at least 3 times in minimum medium No. 7, containing no folic acid.

The assay is based on a turbidimetric determination of the development of *Enterococcus hirae* ATCC 8043, which varies according to the quantity of folic acid present in the culture broth.

The calibration curve necessary for quantitatively determining the folic acid produced is constructed by culturing *Enterococcus hirae* ATCC 8043 in Bacto Folic AOAC Medium (Difco, USA [0967-15]).

To said medium, which contains all the nutrilites necessary for development, with the exception of folic acid, incremental quantities of folic acid are added (0, 1, 2, 4, 6 and 8 ng per tube containing 10 ml of culture broth).

In parallel, *Enterococcus hirae* ATCC 8043 is inoculated into tubes of Bacto Folic AOAC Medium, to which different quantities of the surnatant of the fermentation broth of strain DSM 16594 are added.

After all the tubes have been incubated at 37° C. for 16-18 hours, a turbidimetric reading is taken of the samples at 600 nm and a line graph is drawn on a semi-logarithmic scale by plotting the log of the folic acid concentration according to the optical density of the sample.

Preparation of the Standard Solution (S.S.) of Folic Acid at a Concentration of 2 µg/l, i.e. 2 ng/ml.

Dissolve 50 mg of folic acid in approximately 30 ml of NaOH 0.01N and 300 ml of $H_2O$. Correct the pH to 7.5 using diluted HCl (0.1N) and bring the volume to 500 ml by adding $H_2O$. Add 2 ml of the above-described solution to 50 ml of $H_2O$, correct the pH to 7.5 and bring the volume to 100 ml by adding $H_2O$ (s.s. of 2 µg/ml).

Dilute 1 ml of this solution to 1 liter with $H_2O$ so as to obtain the s.s. of 2 ng/ml (2 µg/l).

Preparation of Tubes Containing Bacto Folic Acid Medium

Dissolve 11 g of the starting powder in 100 ml of $H_2O$. To dissolve the components completely, boil the medium for 2-3 minutes. Dispense 5 ml aliquots into the tubes after rinsing the latter several times with distilled water. Add different aliquots of the fermentation broth surnatant or the s.s. of folic acid (2 ng/ml) and then add $H_2O$ to bring the final volume of each tube to 10 ml. Sterilize at 1210 for 5'.

| | | | | | | | |
|---|---|---|---|---|---|---|---|
| ng of folic acid per tube | 0 | 1 | 2 | 4 | 6 | 8 | 10 |
| ml of s.s. 2 ng/ml | 0 | 0.5 | 1 | 2 | 3 | 4 | 5 |
| ml of $H_2O$ | 5 | 4.5 | 4 | 3 | 2 | 1 | 0 |
| µg of folic acid per l | 0 | 0.1 | 0.2 | 0.4 | 0.6 | 0.8 | 1 |

4 ml of water and 1 ml of fermentation broth surnatant, obtained by centrifugation and filtration with a 0.22µ filter followed by appropriate dilution, are added to the other 2 tubes.

A tube containing no folic acid is prepared as a blank sample; it is not inoculated.

Preparation of the Inoculum

Two days before the assay, a fresh stab culture of *Enterococcus hirae* ATCC 8043 is inoculated into a tube containing M17 liquid medium (Bacto M17 Broth, Difco Laboratories, USA [1856-17]). To prepare the culture that will be used as inoculum, the culture in M17 is sterilely centrifuged, the surnatant is eliminated and the cells are washed 3 times with 9 ml of physiological solution. The cell pellet is again suspended in 9 ml of physiological solution and 1 ml of this bacterial suspension is added to 100 ml of sterile physiological solution contained inside an Erlenmeyer flask. One drop of this suspension is added to a tube of Bacto Folic AOAC Medium, to which 10 ng of folic acid is also added, and the tube is incubated at 37° C. without being shaken.

On the day of the test, the culture prepared according to the above-described procedure is used to prepare the test inoculum: the culture is sterilely centrifuged, the surnatant is eliminated and the cells are washed 3 times with 9 ml of physiological solution. The cells are again suspended in 9 ml of physiological solution and 1 ml of this bacterial suspension is added to 100 ml of sterile physiological solution contained inside an Erlenmeyer flask. To inoculate the test tubes, 1 drop of this suspension is added to all the tubes sterilized at 121° C. for 5'.

The tubes are subsequently incubated at 37° C. for 16-18 hours.

Productivity in Pure Culture

The folic acid produced by strain DSM 16594 in minimum medium No. 7 amounts to 56-62 ng/ml.

The tests yield constant, reproducible results when conducted both on cultures in the absence of pH control and on cultures in bioreactors with a constant pH.

As a rule, the pH of the substances contained in the colon may vary considerably, in relation to certain pathologies or dietary factors. The production of folic acid by DSM 16594 showed be constant (approximately 57-60 ng/ml) regardless of the measured pH value, which in this case ranged from 5.5 to 7.0.

It was also observed that strain DSM 16594 produces folic acid without being affected by negative feedback, hence to a degree that is wholly independent of the concentration of folic acid present in intestinal contents. In fact, strain DSM 16594 was also cultured in minimum medium No. 7 in the presence of increasing concentrations of folic acid (0, 1, 2, 5, 10 and 20 ng/ml) and it was observed that the strain always synthesizes and secretes constant quantities of folic acid (58-61 ng/ml), which are thus added to those already present in the medium. This aspect is highly important because it suggests that, after strain DSM 16594 is ingested as a probiotic, there may be, within the colon, a continuous supply of folic acid, a vitamin that is indispensable for the rapid turnover metabolism of enterocytes. The metabolic deregulation of strain DSM 16594, i.e. the absence of a control mechanism that blocks the biosynthesis of folic acid where sufficient quantities of the latter are already present, is confirmed by the fact that the quantity of folic acid produced is at least 50 times greater than the amount necessary to assure the healthy development of bacteria which do not synthesize this vitamin and must thus obtain it from outside sources in order to develop adequately.

Evaluation of the Contribution of Folic Acid Provided by Strain DSM 16594 in Fecal Cultures In order to evaluate whether there was an effective production of folic acid by strain DSM 16594 in mixed cultures, i.e. cultures simulating the composition of intestinal microflora, fecal cultures were prepared, i.e. cultures inoculated with diluted fecal samples, which may or may not have been inoculated with strain DSM 16594; in said cultures the increase in folic acid concentration was determined.

The mixed cultures used were inoculated with fecal samples diluted so as to simulate the normal microbial composition of intestinal contents. The culture medium used contains 10 ng/ml of folic acid, a quantity such as to ensure the development of the entire inoculated microbial population. The medium also contains peptones, vitamins and fructo-oligosaccharides (FOS) as a source of carbon.

The choice of FOS is due to the fact that the intake of a probiotic *bifidobacterium* in combination with this prebiotic carbohydrate, i.e. one that is neither digested nor absorbed and is thus able to reach the colon, where it is prevalently metabolized by bifidobacteria, favors the colonization of the intestine by both the probiotic *bifidobacterium* and endogenous bifidobacteria.

Fecal Cultures

The fecal cultures were grown in a medium prepared according to the procedures described previously and having the following composition:

| | |
|---|---|
| Raftilose P95 (FOS) (Orafti Group, Tienen, Belgium) | 20 g/L |
| Vitamin Assay Casaminoacids (DIFCO Laboratories, USA [0288-17] | 5 g/L |
| Cysteine | 0.5 g/L |
| Folic acid | 10 µg/L |
| Solution A | 700 ml/L |
| Solution B | 1 ml/L |
| Solution C | 1 ml/L |
| Solution D | 5 ml/L |
| Solution E | 10 ml/L |

| Solution A | |
|---|---|
| $(NH_4)_2SO_4$ | 10 g |
| Sodium acetate | 10 g |
| Ascorbic acid | 10 g |
| $KH_2PO_4$ | 1 g |
| $MgSO_4$ | 0.7 g |
| NaCl | 0.2 g |
| Tween 80 | 1 ml |

The Tween 80 is dissolved in 700 ml of boiling distilled water; thereafter all the other components are added in sequence.

| Solution B | |
|---|---|
| Boric acid | 25 mg |
| $CuSO_4$ | 2 mg |
| KI | 5 mg |
| $FeCl_3$ | 10 mg |
| $MnSO_4$ | 20 mg |
| Sodium molybdate | 10 mg |
| $ZnSO_4$ | 20 mg |

These components are dissolved in sequence in 50 ml of distilled water at room temperature.

| Solution C | |
|---|---|
| Biotin | 0.2 mg |
| Calcium pantothenate | 40 mg |
| Niacin | 40 mg |
| P-aminobenzoic acid | 20 mg |
| Pyridoxine | 40 mg |
| Riboflavin | 20 mg |
| Thiamine | 40 mg |

These components are dissolved in sequence in 100 ml of distilled water at room temperature.

| Solution D | |
|---|---|
| $FeSO_4$ | 50 mg |

The salt is dissolved in 25 ml of distilled water at room temperature.

Solution E 50 mg/L of hemin (Sigma-Aldrich SRL, Via Gallarate, Milan, Italy [H5533]) is dissolved in 5 ml of NaOH 1M and distilled water is added to bring the volume to 1 liter.

Method 40 ml aliquots of medium are dispensed into 100 cc bottles with a perforable rubber cap. The rubber caps are perforated with a needle and the bottles are placed in a boiling water bath. After 10 minutes of incubation at 100° C. the cap is punctured with a second needle, through which nitrogen is insufflated into the bottle for 10 minutes at a pressure of 0.15 bars. Once the insufflation has been accomplished, both needles are removed and the bottles are sterilized at 110° C. for 30'.

Preparation of the Inoculum

A fresh fecal sample is transferred into an anaerobic chamber (10% $H_2$, 10% $CO_2$, 80% $N_2$).

A 10% suspension is then prepared in the above-described medium and homogenized with sterile glass beads having a diameter of 3 mm.

From this suspension a 1:100 dilution is prepared in the same medium contained in the bottles. 0.4 ml of the latter dilution is inoculated with a syringe into two sterile bottles containing 40 ml of culture medium.

Comparison of Folic Acid Present in Fecal Samples Inoculated or not Inoculated with Strain DSM 16594.

One of the two identical samples inoculated with the diluted fecal sample is also inoculated with 0.4 ml of a culture of strain DSM 16594 made to develop for 24 hours in minimum medium no. 7. Both fecal cultures, one of which is also inoculated with strain DSM 16594 and the other of which is not, are incubated at 37° C. for 24 hours.

After this time has elapsed, an aliquot of both cultures is centrifuged at 3500 g for 10' and the surnatant is filtered with a 0.4 µm filter. The supernatants, diluted accordingly, are used for the microbiological assay of folic acid.

Folic Acid Productivity in the Fecal Cultures

The concentration of folic acid in the fecal cultures not inoculated with strain DSM 16594 ranges approximately from 30 to 70 ng/ml.

The matching cultures inoculated with strain DSM 16594 showed a significant increase in folic acid concentration. Said increase ranged from 30 to 50 ng/ml, a quantity which was thus added to the previously indicated 30-70 ng/ml.

This latter finding further demonstrates that the administration of the probiotic bacterial strain of the present invention, DSM 16594, can ensure the presence of high levels of folic acid in the colon regardless of the patient's health condition.

As a result, the reestablishment and maintenance of an optimal balance of intestinal bacterial flora may be facilitated and assured.

The previous experimental section described in detail the use of one of the particularly preferred bacterial strains of the present invention, i.e. strain DSM 16594.

Identical trials were conducted, in the same experimental conditions and using the same quantities of reagents, also on the other four preferred bacterial strains of the present invention, namely DSM 16595, DSM 16596, DSM 16597 and DSM 16598.

It was demonstrated that these bacterial strains produce folic acid in the same manner and with the same characteristics as strain DSM 16594.

The productivity of *Bifidobacterium adolescentis* DSM 16595, *Bifidobacterium breve* DSM 16596, *Bifidobacterium pseudocatenulatum* DSM 16597 and *Bifidobacterium pseudocatenulatum* DSM 16598 showed to be lower in comparison to that of *Bifidobacterium adolescentis* DSM 16594.

In particular, DSM 16595 produces approximately 30.5%, DSM 16596 approximately 13%, DSM 16597 25.5% and DSM 16598 28% of the amount of folic acid produced by DSM 16594.

Nonetheless, in these cases as well, the quantity of folic acid produced (amounting, respectively, to approximately 16-20 ng/ml for DSM 16595; 6-9 ng/ml for DSM 16596; 14-16 ng/ml for DSM 16597 and 14-19 ng/ml for DSM 16598) is significantly higher (approximately 14 to 16 times higher for DSM 16595; 5 to 7 times higher for DSM 16596; 12 to 13 times higher for DSM 16597 and 12 to 15 times higher for DSM 16598) than the amount needed to ensure the healthy development of other bacteria which require this vitamin for optimal development.

REFERENCES

1. Fuchs C. S. et al. (2002) The influence of folate and multivitamin use on the familial risk of colon cancer in women. *Cancer Epidemiol. Biomark. Prev.* 11, 227-234.
2. Ma J. et al. (1999) A polymorphism of the methionine synthase gene: association with plasma folate, vitamin B12, homocyst(e)ine, and colorectal cancer risk. *Cancer Epidemiol. Biomark. Prev.* 8, 825-829.
3. Hartemink R., Kok BIFIDOBACTERIUMJ. Weenk G. H., Rombouts F. M. (1996) Raffinose-*Bifidobacterium* (RB) agar, a new selective medium for bifidobacteria *J. Microbiol. Methods.* 27, 33-43.
4. Scardovi V. Crociani F. (1974) *Bifidobacterium catenulatum, Bifidobacterium dentium, Bifidobacterium angulatum*: three new species and their deoxyribonucleic acid homology relationships. *Int. J. Syst. Bacteriol.* 24, 6-20.

What is claimed is:

1. A *Bifidobacterium* strain of folic acid producing probiotic bacteria of human origin selected from the group consisting of:

*Bifidobacterium adolescentis* DSM 16594, *Bifidobacterium adolescentis* DSM 16595, *Bifidobacterium breve* DSM 16596, *Bifidobacterium pseudocatenulatum* DSM 16597, and *Bifidobacterium pseudocatenulatum* DSM 16598.

2. A *Bifidobacterium* strain according to claim 1, wherein said strain is *Bifidobacterium adolescentis* DSM 16594.

3. A *Bifidobacterium* strain according to claim 1, wherein said strain is *Bifidobacterium adolescentis* DSM 16595.

4. A *Bifidobacterium* strain according to claim 1, wherein said strain is *Bifidobacterium breve* DSM 16596.

5. A *Bifidobacterium* strain according to claim 1, wherein said strain is *Bifidobacterium pseudocatenulatum* DSM 16597.

6. A *Bifidobacterium* strain according to claim 1, wherein said strain is *Bifidobacterium pseudocatenulatum* DSM 16598.

7. A pharmaceutical, veterinary or food formulation comprising one or more of the *Bifidobacterium* strains according to claim 1.

8. A formulation according to claim 7, comprising two or more of the strains according to claim 1.

9. A formulation according to claim 7, further comprising one or more probiotic bacterial strains having complementary characteristics, wherein said probiotic bacterial strains are selected from the group consisting of:

*Lactobacillus acidophilus* LMG P-21381;
*Lactobacillus casei* subsp. *paracasei* LMG P-21380;
*Lactobacillus plantarum* LMG P-21021;
*Lactobacillus pentosus* LMG P-21019;
*Lactobacillus plantarum* LMG P-21020;

*Lactobacillus plantarum* LMG P-21022;
*Lactobacillus plantarum* LMG P-21023;
*Bifidobacterium lactis* LMG P-21384;
*Streptococcus delbrueckii* subsp. *thermophilus* DSM 16506;
*Streptococcus delbrueckii* subsp. *thermophilus* DSM 16507;
*Bifidobacterium longum* DSM 16603;
*Bifidobacterium breve* DSM 16604; and
*Lactobacillus casei* subsp. *rhamnosus* DSM 16605.

10. A formulation according to claim 7, further comprising other substances having prebiotic characteristics, wherein said substances having prebiotic characteristics are selected from the group consisting of:
fructo-oligosaccharides (FOS), inulin, isomalto-oligosaccharides, resistant starch, pectin, galacto-oligosaccharides, arabinogalactan, xylo-oligosaccharides, glucomannan and chitosan oligosaccharides.

11. A formulation according to claim 9, further comprising other substances having prebiotic characteristics, wherein said substances having prebiotic characteristics are selected from the group consisting of:
fructo-oligosaccharides (FOS), inulin, isomalto-oligosaccharides, resistant starch, pectin, galacto-oligosaccharides, arabinogalactan, xylo-oligosaccharides, glucomannan and chitosan oligosaccharides.

12. A formulation according to claim 7, further comprising an additive, a vehicle, an excipient, a flavoring, or a stabilizer, wherein said additive is selected from the group consisting of: amino acids, vitamins, antioxidants, enzymes, glutamine, arginina, superoxide dismutase, and glutathione.

13. A formulation according to claim 7, wherein said one or more strains is present in freeze-dried form.

14. A formulation according to claim 7, containing from $10^5$ to $10^{11}$ of cells of said one or more strains per single dose.

15. A formulation according to claim 7, in the form of a capsule, an oral solution or suspension, a powder in a packet, a tablet, a suppository, a vaginal tablet or a pessary.

16. A *Bifidobacterium* strain according to claim 1, wherein said strain is provided as a probiotic in a food product, or is provided in a product derived from milk or its derivatives, or is provided in combination with a prebiotic substance, or is provided in a symbiotic food preparation.

* * * * *